(12) United States Patent
Deschaseaux et al.

(10) Patent No.: US 9,375,464 B2
(45) Date of Patent: Jun. 28, 2016

(54) HLA-G ISOFORM FOR USE IN THE TREATMENT OF A DISEASE ASSOCIATED WITH BONE RESORPTION

(75) Inventors: Frédéric Deschaseaux, Tours (FR); Luc Sensebe, Joue les Tours (FR); Nathalie Rouas-Freiss, Paris (FR)

(73) Assignees: Etablissement Francais du Sang, Saint Denis (FR); Commissariat a l'Energie Atomique et aux Energies Alternatives, Paris (FR)

(*) Notice: Subject to any disclaimer, the term of this patent is extended or adjusted under 35 U.S.C. 154(b) by 144 days.

(21) Appl. No.: 13/989,303

(22) PCT Filed: Nov. 23, 2011

(86) PCT No.: PCT/IB2011/055255
§ 371 (c)(1),
(2), (4) Date: Aug. 13, 2013

(87) PCT Pub. No.: WO2012/070003
PCT Pub. Date: May 31, 2012

(65) Prior Publication Data
US 2014/0065184 A1 Mar. 6, 2014

(30) Foreign Application Priority Data
Nov. 23, 2010 (FR) ..................... 10 59653

(51) Int. Cl.
*A61K 38/17* (2006.01)
*A61P 19/08* (2006.01)
*A61K 39/00* (2006.01)

(52) U.S. Cl.
CPC ............. *A61K 39/0005* (2013.01); *A61K 38/17* (2013.01); *A61K 38/1774* (2013.01)

(58) Field of Classification Search
None
See application file for complete search history.

(56) References Cited

U.S. PATENT DOCUMENTS

| 2007/0020703 A1* | 1/2007 | Menier et al. ................ 435/7.21 |
| 2011/0135672 A1* | 6/2011 | Horuzsko ............ C07K 16/248 424/185.1 |

FOREIGN PATENT DOCUMENTS

| FR | 2760023 | 8/1998 |
| WO | 2008/051568 | 5/2008 |
| WO | 2011/061726 | 5/2011 |

OTHER PUBLICATIONS

Carosella et al., Blood, 2008, vol. 111(10):4862-4870.*
Ongaro, Human Leukocyte Antigen-G Molelcules are Constitutively Expressed by Synovial Fibroblasts and Upmodulated in Osteoarthritis, Human Immunology, 71, pp. 342-350, 2010.
Selmani, Human Leukocyte Antigen-G5 Secretion by Human Mesenchymal Stem Cells is Required to Suppress T Lymphocyte and Natural Killer Function and to Induce CD4+CD25higherFOXP3+ Regulatory T Cells, Stem Cells, 26, pp. 212-222, 2008.
Lorenzo, Osteoimmunology: Interactions of the Bone and Immune System, Endocrine Reviews, 29, pp. 403-440, 2008.
Deschaseaux, The Human Non-Classical Type I CMH HLA-G Proteins Show Restricted Expression by Osteoblastic Lineage in Normal and Tumoral Conditions, Bone, 48, p. S109, 2011.
Uccelli, Mesenchymal Stem Cells in Health and Disease, Nature Reviews, 8, pp. 726-736, 2008.

* cited by examiner

*Primary Examiner* — Xiaozhen Xie
(74) *Attorney, Agent, or Firm* — Morgan, Lewis & Bockius LLP

(57) ABSTRACT

Novel use of HLA-G isoforms in the treatment or prevention of diseases in which bone resorption is observed.

7 Claims, 7 Drawing Sheets

Figure 1:
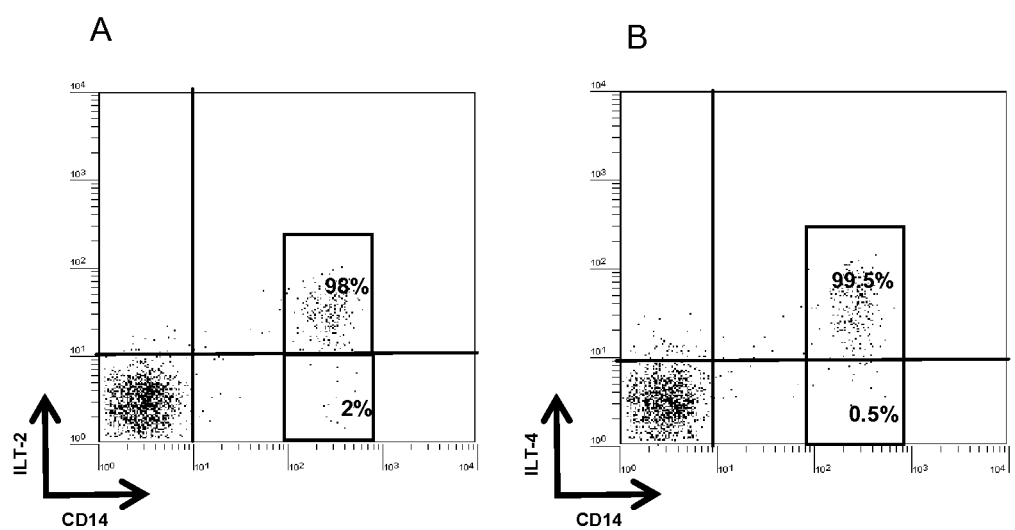

HLA-G ISOFORM FOR USE IN THE TREATMENT OF A DISEASE ASSOCIATED WITH BONE RESORPTION

The present invention relates to a novel use of HLA-G isoforms as agents limiting bone resorption, for the treatment, for example, of osteoporosis.

Antigens of the major histocompatibility complex (MHC) can be divided into several classes: the class I antigens (HLA-A, -B and -C) which have 3 globular domains ($\alpha 1$, $\alpha 2$ and $\alpha 3$), and of which the $\alpha 3$ domain is associated with $\beta 2$ microglobulin, the class II antigens (HLA-DP, -DQ and -DR) and the class III antigens (complement). The class I antigens comprise, in addition to the abovementioned antigens, other antigens termed nonclassical class I antigens (class Ib) and in particular the antigens HLA-E, HLA-F and HLA-G (Carosella et al., 2008a).

The nucleotide sequence of the HLA-G gene (also called HLA-6.0 gene) was described by Geraghty et al. in 1987: it comprises 4396 base pairs and exhibits an intron/exon organization homologous to that of the HLA-A, -B and -C genes. This HLA-G gene comprises 8 exons, 7 introns and an untranslated 3' end. It differs from the other genes encoding the class I antigens in that the in-phase translation termination codon is located at the level of the second codon of exon 6; consequently, the cytoplasmic region of the protein encoded by this gene is shorter than that of the cytoplasmic regions of the HLA-A, -B and -C proteins. Ishitani and Geraghty (1992) have shown that the primary transcript of the HLA-G gene may be spliced in several ways and produces at least three distinct mature mRNAs: the primary transcript of HLA-G provides a complete copy G1 of 1200 bp, a fragment of 900 bp G2) and a fragment of 600 bp (G3). The G1 transcript does not comprise exon 7 and corresponds to the sequence described by Ellis in 1990, that is to say that it encodes a protein which comprises a signal sequence, 3 outer domains, a transmembrane region and a cytoplasmic sequence. The mRNA G2 does not comprise exon 3, that is to say that it encodes a protein in which the $\alpha 1$ and $\alpha 3$ domains are directly joined. The mRNA G3 contains neither exon 3 nor exon 4, that is to say that it encodes a protein in which the $\alpha 1$ domain and the transmembrane sequence are directly joined. The splicing which prevails for the production of the G2 antigen causes the joining of an adenine (A) (obtained from the $\alpha 1$ coding domain) with an adenine-cytosine (AC) sequence (derived from the $\alpha 3$ coding domain), which causes the creation of an AAC (asparagine) codon in place of the GAC (aspartic acid) codon, present in the 5' position of the sequence encoding the $\alpha 3$ domain in HLA-G1. The splicing generated for the production of HLA-G3 does not cause the formation of a new codon in the splicing region.

The existence of other spliced forms of HLA-G mRNA has also been shown: the G4 transcript, which does not include exon 4; the G5 transcript which includes intron 4 between exons 4 and 5, thus causing a modification of the reading frame during the translation of this transcript and in particular the appearance of a stop codon after amino acid 21 of intron 4; the G6 transcript having intron 4 but having lost exon 3 and finally the G7 transcript which includes intron 2 thus causing a modification of the reading frame during the translation of this transcript and the appearance of a stop codon after amino acid 2 of intron 2 (Kirszenbaum et al., 1994 and 1995; Moreau et al., 1995; patent application EP 0 677 582).

There are therefore at least 7 different HLA-G mRNAs which encode 7 isoforms of HLA-G, of which 4 are membrane isoforms (HLA-G1, -G2, -G3 and -G4) and 3 are soluble isoforms (HLA-G5, -G6 and -G7) (Carosella et al., 2008b).

HLA-G was initially described as being specifically spliced by the trophoblaste at the level of the placental barrier at the feto-maternal interface (Carosella et al., 2008a). It was also recently detected in the thymus, the cornea, the endothelial precursors, in the mesenchymal stem cells (also called bone marrow stromal cells or bone marrow multipotent stromal cells, and noted MSC) and in normal or tumoral osteoblasts (Deschaseaux et al., 2009a). However, HLA-G mRNAs are detected in practically all the cells of the body at a basal level which may be amplified and whose translation into protein is induced under the effect of DNA demethylating agents, of some cytokines such as IFN (interferon), of stress factors or of hypoxia (Carosella et al., 2008a). Thus, under specific conditions such as the transplantation of a tissue, the development of certain tumors or an inflammatory response, the HLA-G protein may be expressed in tissues which do not express it under normal conditions. In the blood, both the membrane isoforms detached from the membranes, such as HLA-G1 (which are then called HLA-G1s for "HLA-G1 shedding") and the other soluble isoforms are found.

HLA-G is distinguishable from the other class I HLA molecules insofar as:
its expression is restricted to certain tissues,
it exhibits very little polymorphism (44 alleles encoding 15 protein variants), this being due to numerous silent mutations, and
it induces immune tolerance.

This immune tolerance can be explained by several mechanisms: HLA-G inhibits the activation of NK cells via its binding to the ILT2 (CD85j) and KIR2DL4 (CD158d) receptors. ILT2 is also expressed by the monocytic cells, the dendritic cells, the B and T lymphocytes and the macrophages (Carosella et al., 2008a; Rouas-Freiss et al., 2007). By binding to the ILT2 receptor, HLA-G is capable of inhibiting the proliferation of T lymphocytes ($CD4^+$ and $CD8^+$) as well as their cytotoxic potential and can induce the formation of suppressor or regulatory lymphocytes (Barrow and Trowsdale, 2006; Le Maoult et al., 2005; Naji et al. 2007a). HLA-G also binds to ILT4 (CD85d) expressed on cells of the myeloid type, namely the monocytes and the dendritic cells. The binding of HLA-G to ILT2 and/or ILT4 causes the inhibition of the maturation of the dendritic cells and the generation of dendritic cells of the tolerogen type. The ILT2 and ILT4 receptors are transmembrane molecules having a long cytoplasmic fragment containing ITIM motifs or "Immunoreceptor Tyrosine-based Inhibitory Motifs". They induce the inhibition of cellular activation by the recruitment of SHP-1 or SHP-2 phosphatases through a hyperphosphorylation of these proteins (Barrow and Trowsdale, 2006).

The bone tissue constituting the skeleton is constantly renewed during the life of the individual. This renewal mechanism is called bone remodeling. It occurs through a finely regulated balance between bone formation and bone resorption. Whereas bone formation involves the synthesis and the deposition of bone matrix (BM) by the osteoblasts, bone resorption occurs through the degradation of the BM by the osteoclasts (Cohen, 2006).

The osteoblasts are derived from mesenchymal stem cells. They are mononucleated cells present in the growing bone tissue and lining the bone. They express, in a characteristic manner, collagen I (colla1), non-specific alkaline phosphatase (ALPL), parathyroid hormone receptor type I (PTH-R1), osteonectin (SPARC), osteocalcin and osterix transcription factor. The osteoblasts may then become osteocytes embedded in the BM, thus ensuring its maintenance (Deschaseaux et al., 2009b).

The osteoclasts are multinucleated cells expressing the TRAP ("Tartrate Resistant Phosphatase") protein. They are derived from cells of the monocytic line under the action of the soluble RANKL factor ("Receptor Activator of NF-kB Ligand" or TNFSF11) which may be secreted by the osteoblasts themselves but also by cells of the lymphocyte type (Duplomb et al., 2007).

The deregulation of bone modeling causes a number of pathologies in humans (Cohen, 2006). Excess bone formation can lead to osteopetrosis while excess bone resorption is the cause of osteoporosis (disease affecting 19 million Europeans including 1 out of 3 women and 1 out of 8 men; 1.5 million persons in Europe suffer from fracture due to osteoporosis. Data from the association Health First Europe) or more rarely of Paget's disease or of osteolytic tumors (bone metastases from breast or prostate cancer).

In the light of the above, a need therefore exists to have molecules for treating or preventing bone remodeling dysfunctions, in particular for treating osteoporosis.

The principal molecules used for treating osteoporosis are either synthetic chemical molecules belonging to the family of biphosphonates which inhibit the activation of the osteoclasts (e.g., etidronate, clodronate, pamidronate, ibandronate, alendronate and tiludronate; Deschaseaux et al., 2009a), or humanized antibodies (e.g., denosumab) mimicking the action of osteoprotegerin which is a competitive inhibitor of RANKL (Deschaseaux et al., 2009a).

RANKL, also called "TNF-related activation-induced cytokine" (TRANCE), "osteoprotegerin ligand" (OPGL) or "osteoclast differentiation factor" (ODF), is a cytokine which is involved in bone metabolism by inducing the generation of osteoclasts and by activating them (Duplomb et al., 2007).

Osteoprotegerin (OPG) is a soluble receptor, belonging to the family of TNF ("tumor necrosis factor") receptors, to which RANKL binds. The binding of OPG to RANKL blocks the interaction of the latter with the RANK receptor expressed by the osteoclasts and the monocytes (said interaction being responsible for the differentiation and the activation of the osteoclasts). RANKL and OPG therefore play a key role in the differentiation and activation of the osteoclasts (Cohen, 2006; Duplomb et al., 2007; Lorenzo et al., 2008).

The inventors have shown, unexpectedly, that various isolated isoforms of HLA-G, in particular the soluble isoforms, are capable of inhibiting in vitro not only the formation of the osteoclasts whose biological function is to resorb the bone matrix, but also osteoclastogenesis. The isoforms of HLA-G may therefore be used as anti bone-resorption agents.

The aim of the present invention is therefore an isolated isoform of HLA-G for use as a medicament for the treatment or prevention of a disease in which bone resorption is observed.

Among the relevant diseases in which bone resorption is observed, there may be mentioned osteoporosis, osteopenia, bone fractures, Paget's disease and osteolytic tumors.

The expression "isoform of HLA-G" is understood to mean an isoform of HLA-G chosen from the membrane isoforms of HLA-G (i.e., HLA-G1, HLA-G2, HLA-G3 and HLA-G4) and the soluble isoforms of HLA-G (i.e., HLA-G5, HLA-G6 and HLA-G7).

The expression "isolated" is understood to mean an isoform of HLA-G which is separated from a compound or from a medium with which it is naturally associated, for example a cell membrane or the cytoplasm. Thus, when a membrane isoform of HLA-G is used to carry out the present invention, it means that this isoform is separated (isolated) from the cell membrane, such as for example from the cell membrane of a stem cell, in particular a placental stem cell.

By way of example, the membrane isoforms may be advantageously expressed in eukaryotic cells, in accordance with the method described in international application PCT WO 98/37098, and then solubilized by treatment of the membrane (stripping agent, such as papain) and purification, for example on an immunoaffinity column with specific antibodies.

According to a preferred embodiment of the present invention, said isoform of HLA-G is chosen from the group consisting of HLA-G1 and HLA-G5, preferably HLA-G5.

In accordance with the invention, the isoform of HLA-G used is:
  either in a free (or monomeric) form, which may potentially form dimmers in solution,
  or in a multimeric form, in particular in a clustered form on beads (as described by Naji et al., 2007a), so that the HLA-G molecule is in a form of multimers, described as being the functionally optimal confirmation of the HLA-G molecule. Indeed, the HLA-G dimers have been described as having a considerably increased affinity for their receptors compared with the monomers.

The use of an isoform of HLA-G in the treatment of a disease in which bone resorption is observed may constitute an alternative or augmentary treatment in combination with the treatments usually carried out.

The subject of the present invention is also a pharmaceutical composition comprising an isolated isoform of HLA-G as defined above and at least one pharmaceutically acceptable vehicle for the treatment or prevention of a disease in which bone resorption as defined above is observed.

According to a preferred embodiment of said pharmaceutical composition, it does not contain stem cells, in particular placental stem cells.

According to one embodiment of said composition, said pharmaceutically acceptable vehicle is suitable for parenteral administration.

The administration may be for example intravenous, intramuscular or subcutaneous.

According to another advantageous embodiment of said composition, said pharmaceutically acceptable vehicle is suitable for oral administration.

According to another advantageous embodiment of said composition, said pharmaceutically acceptable vehicle is suitable for administration by inhalation.

Solutions or suspensions used for subcutaneous application typically include one or more of the following compounds: a sterile diluent, such as water, for injection, an isotonic and buffered physiological saline solution, or oils, polyethylene glycols, glycerine, polypropylene glycol or other synthetic solvents; antibacterial agents such as benzyl alcohol or methylparabens; antioxidants such as ascorbic acid or sodium bisulfite; chelating agents such as ethylene-diaminetetraacetic acid; buffers such as acetates, citrates or phosphates; and agents for adjusting tonicity such as sodium chloride or dextrose. The pH may be adjusted with acids or bases such as hydrochloric acid or sodium hydroxide.

Such preparations may be provided in the form of ampoules, disposable syringes or multidose vials made of glass or of plastic.

The pharmaceutical compositions suitable for injection include sterile aqueous solutions, sterile dispersions or powders for preparation of sterile injectable solutions or dispersions immediately before use.

For intravenous administration, the preferred vehicles include physiological saline solutions, bacteriostatic water, Cremophor ELTM (BASF, Parsippany, N.J.) or PBS buffer. In all cases, the composition must be sterile and fluid. It must be stable under the conditions for preparation and storage and must comprise preservatives against the contaminating action of microorganisms such as bacteria or fungi.

By way of example, the vehicle may be a solvent or a dispersion medium containing, for example, water, ethanol, a polyol (for example glycerol, propylene glycol or a liquid polyethylene glycol) and mixtures of these compounds.

The appropriate fluidity may be maintained for example using lecithin, or using surfactants. The prevention of the action of microorganisms may be obtained by administering various antibacterial and antifungal agents, for example parabens, chlorobutanol, phenol, ascorbic acid and thimerosal. Said compositions may also include isotonic agents, for example sugars or polyalcohols such as mannitol, sorbitol or sodium chloride.

Prolonged actions of the injectable compositions may be obtained by adding aluminum monostearate or gelatin to the formulation.

The subject of the present invention is also the use of an isoform of HLA-G or of a pharmaceutical composition as defined above for the manufacture of a medicament intended for the treatment or prevention of a disease in which bone resorption as defined above is observed.

The subject of the present invention is also a method for inhibiting bone resorption in a subject requiring it, comprising the administration to said subject of a therapeutically effective quantity of an isoform of HLA-G or of a pharmaceutical composition as defined above.

In addition to the preceding features, the invention comprises other features, which will emerge from the description which follows, which refers to an example showing the in vitro inhibition of osteoclasts by the isoforms of HLA-G, and to the accompanying drawings, in which:

FIG. 1 is a graph showing that only the CD14$^{pos}$ monocytic cells express the ILT2 (A) and ILT4 (B) receptors in cocultures with CD14$^{neg}$ MSC. MSCs of bone marrow of human origin and human peripheral blood monocytic cells were cocultured. After about 6 days, the cells were recovered and labeled with anti-CD14, anti-ILT2 or anti-ILT4 antibodies. They were then analyzed by flow cytometry.

Figure 2:
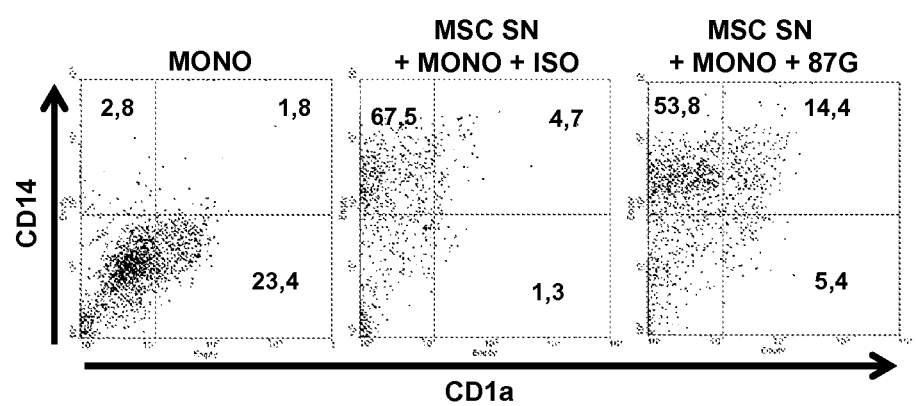

FIG. 2 is a graph showing the action of HLA-G derived from MSC in the inhibition of the differentiation of dendritic cells from peripheral blood monocytes. Monocytic cells of human origin were induced to differentiate into dendritic cells. Fractions of these cells were cultured with supernatants derived from MSC cultures (MSC SN) to which antibodies blocking 87G (MSC SN+MONO+87G) or a controlled antibody of the same isotype as 87G (MSC SN+MONO+ISO) was added. Another fraction of monocytic cells was induced to differentiate without the addition of supernatant or of antibody (MONO). After 6 days of culture, the cells were harvested and analyzed by flow cytometry for the expression of monocytic markers (CD14) and dendritic markers (CD1a). 23% of the monocytic cells differentiated into dendritic cells (CD14$^{neg}$/CD1a$^{pos}$) under the control conditions (MONO). Most of the cells cultured with MSC supernatant and a control antibody are CD14$^{neg}$/CD1a$^{neg}$ whereas a fraction of the CD14$^{pos}$ cells coexpress CD1a under the conditions comprising the anti HLA-G antibody blocking 87G (MSC SN+MONO+87G). The presence of HLA-G in the MSC supernatants therefore inhibited the differentiation of the monocytes into dendritic cells. The blocking of HLA-G by a specific antibody made it possible to restore the differentiation of the monocytes into an intermediate CD14$^{pos}$ CD1a$^{pos}$ population.

Figure 3:
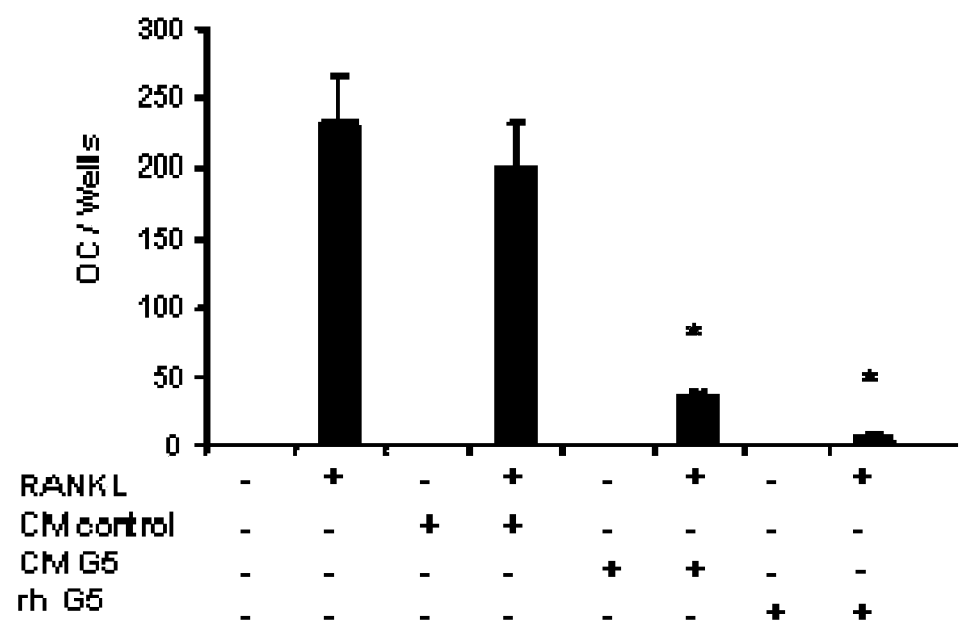
Figure 3:
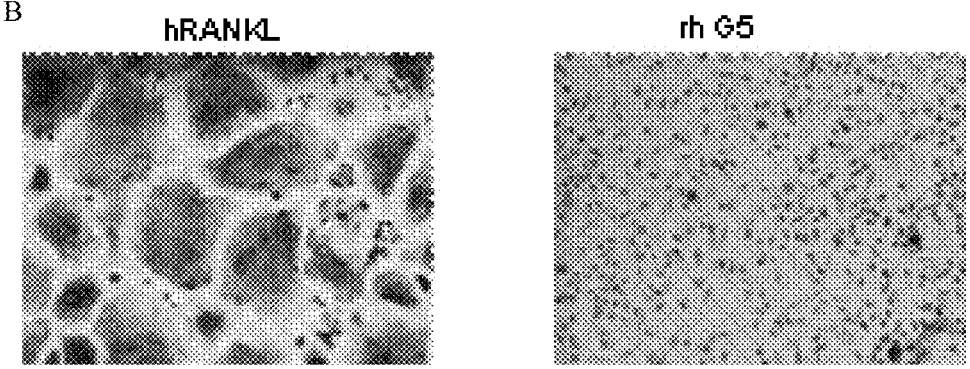

FIG. 3 shows the inhibition of osteoclasto-genesis by HLA-G5. CD14$^{pos}$ monocytic cells of peripheral blood of human origin were induced to differentiate into osteoclasts by the addition of M-CSF and of RANKL (RANKL, positive control). In some assays, medium conditioned with the M8 line (HLA-G$^-$ melanoma cells) transfected either with a vector containing a cDNA encoding HLA-G5 (MC G5) or with a control vector containing no cDNA encoding HLA-G5 (control MC) was added. In another assay, the purified recombinant HLA-G5 protein (rh G5) was added. After 20 days of culture, the TRAP$^{pos}$ multinucleated adherent cells were counted and reported as number of osteoclasts per well (OC/wells) (see graph A). Osteoclasts were detected under the control conditions in the presence of RANKL (photograph B "hRANKL") unlike the conditions containing the supernatant of the M8-HLA-G5 line or containing recombinant HLA-G5 (photograph B "rh G5"). The symbol * indicates that the differences are significant (p<0.01).

Figure 4:
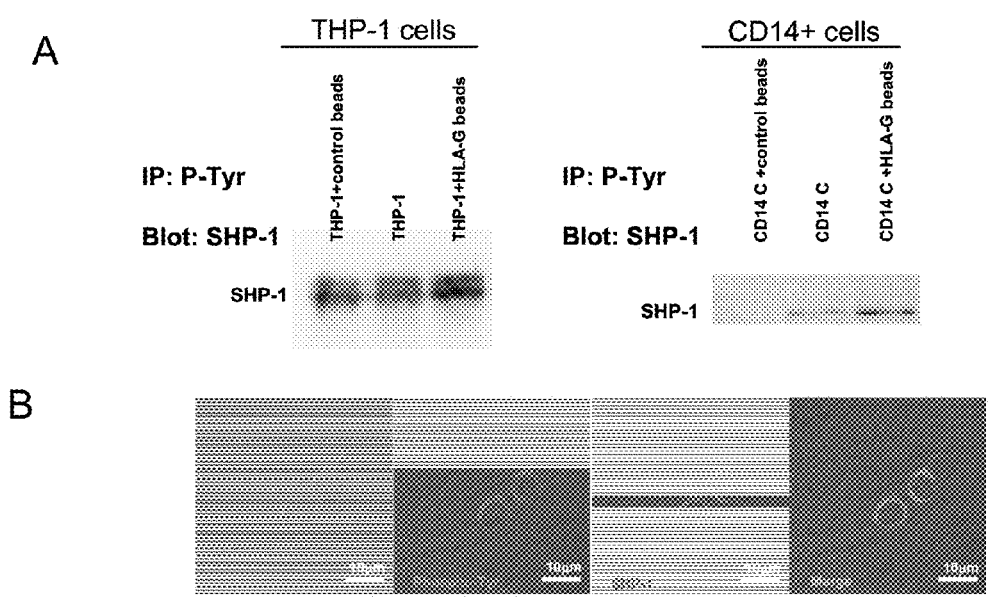

FIG. 4 shows the phosphorylation of SHP-1 in monocytic cells. (A): monocytic cells derived from the THP-1 line ("THP-1 cells") or CD14$^{pos}$ cells of peripheral blood ("CD14+ cells" or CD14 C) were incubated with or without magnetic beads coated either with a control antibody ("control beads") or with HLA-G5 ("HLA-G beads"). The cells were then lysed and used for immunoprecipitation with an anti-phosphorylated tyrosine antibody (IP: P-Tyr). After elution, the complexes retained by the column were separated by electrophoresis and transferred onto a PVDF membrane. The phosphorylated SHP-1 protein was then visualized with an anti-SHP-1 antibody. (B): CD14$^{pos}$ cells of peripheral blood were deposited on a confluent layer of MSC and then fixed, permeabilized and incubated with anti-phosphorylated tyrosine antibodies (2$^{nd}$ photograph from the left) and anti-SHP-1 antibodies (3$^{rd}$ photograph from the left). The 1$^{st}$ photograph from the left represents the cells in the absence of incubation with the antibodies. The 4$^{th}$ photograph from the left represents the fusion of the 2$^{nd}$ and 3$^{rd}$ photographs. The preparation was then examined with a phase contrast confocal microscope; magnification X630. In the presence of HLA-G, the phosphatase SHP-1 is recruited, which results in hyper-phosphorylation of its tyrosine residues.

Figure 5:
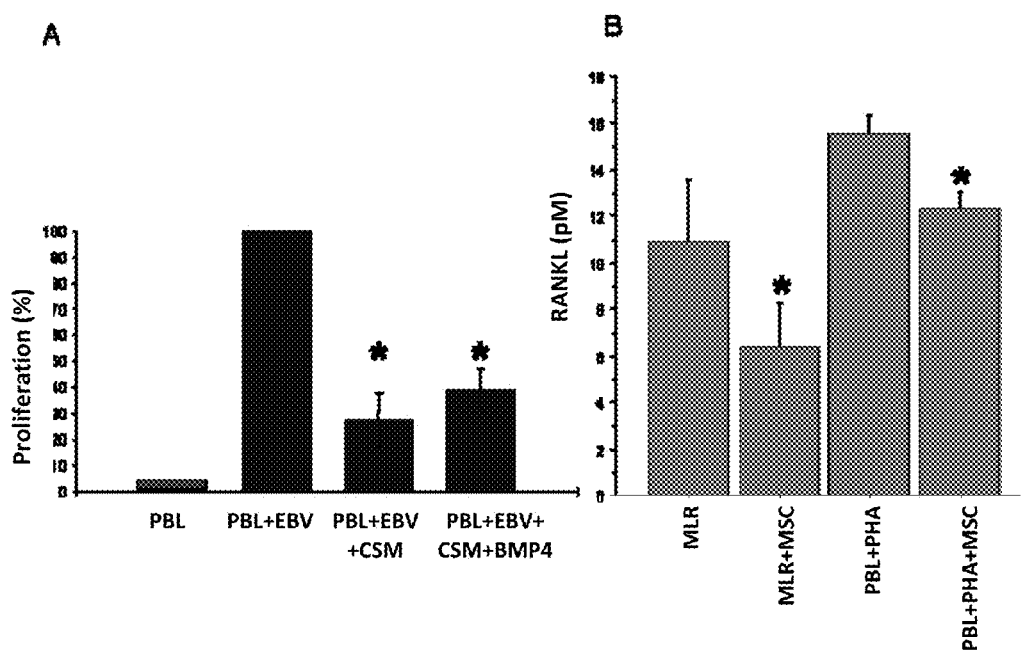

FIG. 5 shows the capacity of MSCs to inhibit lymphocyte proliferation and to reduce the secretion of RANKL by the activated lymphocytes. (A): mixed lymphocyte cultures (MLR) prepared in 96-well plates and comprising peripheral blood lymphocytes (PBL or responding cells) and irradiated B-EBV cells (activating cells) were prepared with MSCs in a third party (that is to say cells obtained from an allogenic donor) in the presence or otherwise of BMP4 (20 ng/ml on D0 and D3). After 6 days of coculture, the lymphocyte proliferation is monitored by reading the fluorescence with a fluorimeter. The various conditions tested were: PBL alone (negative control); PBL+B-EBV (positive control); PBL+B-EBV+MSC; PBL+B-EBV+BMP4; PBL+B-EBV+MSC+BMP4. Number of experiments performed: n=3. (B): peripheral blood lymphocytes (PBL) were activated either with B-EBV cells (MLR condition) or with a mitogen (phytohemagglutinin, PHA) (PBL+PHA) in the presence or otherwise of MSC. After 6 days of culture, the supernatants were recovered and the secreted RANKL was assayed therein by ELISA (results reported in pM). The symbol * indicates that the differences are significant (p<0.05). Number of experiments performed: n=3.

Figure 6:
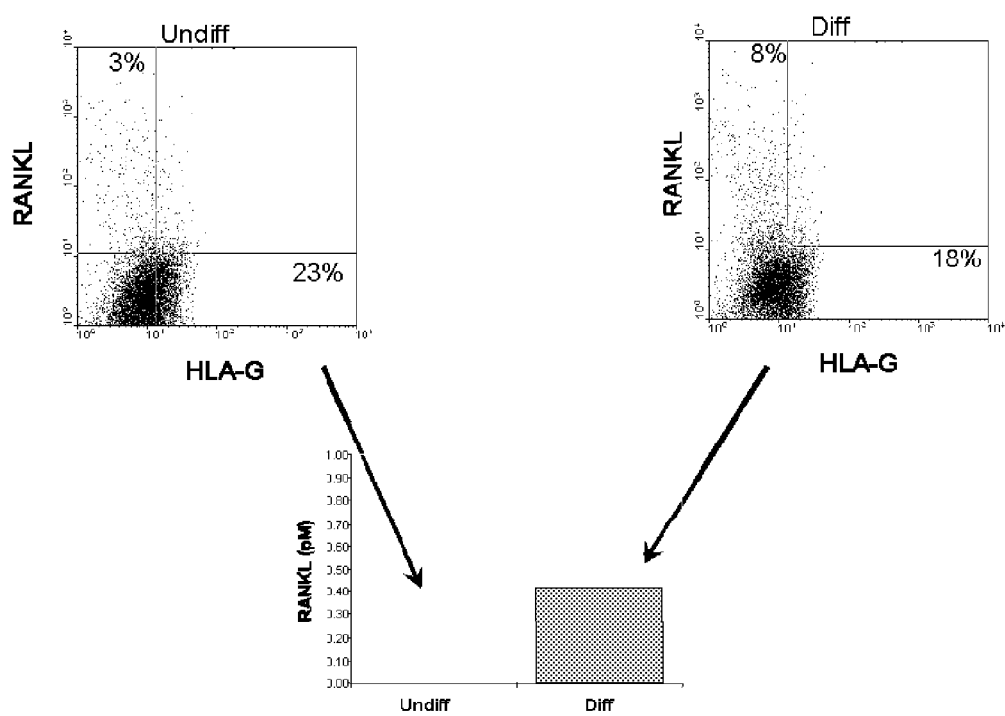

FIG. 6 shows that the MSCs secreting RANKL are HLA-G negative. MSCs were induced to differentiate (Diff) in order to secrete RANKL or were not induced (Undiff). The cells were then incubated with anti-RANKL and anti-HLA-G antibodies (87G) and then analyzed by flow cytometry in order to quantify the simultaneous expression of RANKL and HLA-G (intracellular and membrane isoforms). The supernatants were also recovered and the quantity of RANKL secreted was assayed by ELISA (resulted reported in pM). Number of experiments: n=3.

Figure 7:
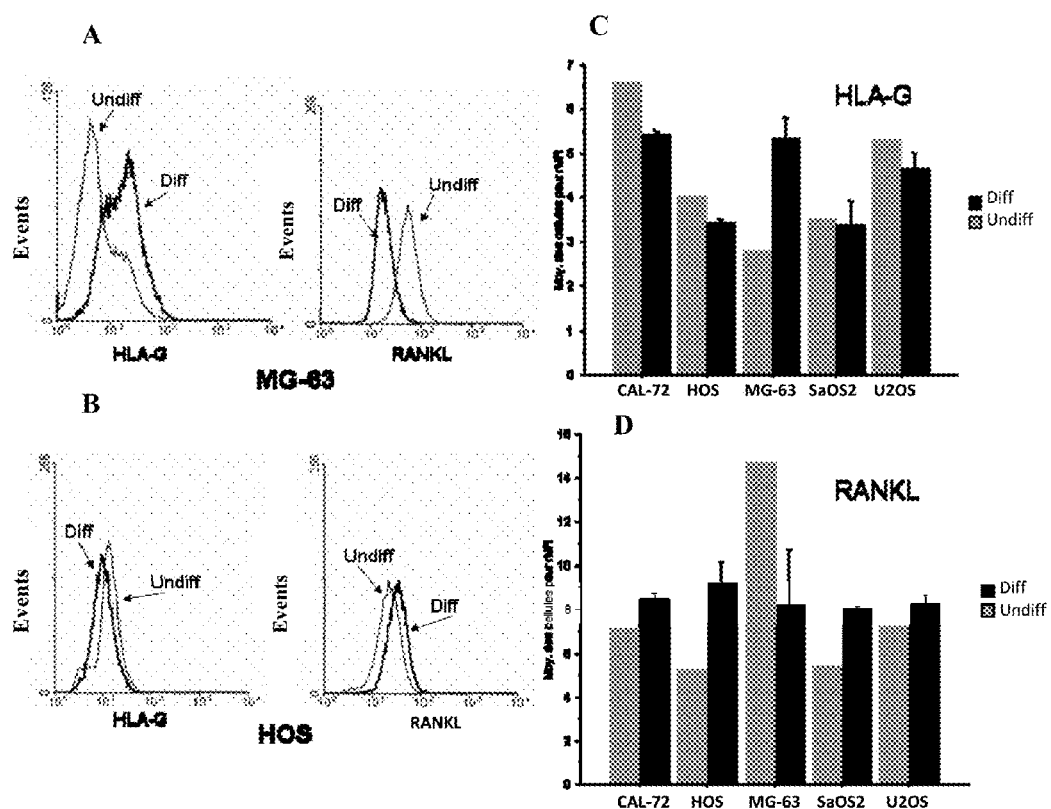

FIG. 7 shows the inverse expressions between HLA-G and RANKL in osteoblastic lines derived from osteosarcomas. Various osteoblastic lines of osteosarcomas (CAL-72, HOS, MG-63, SaOs2 and U2OS) were induced to differentiate (Diff) or otherwise (Undiff). These lines were clearly defined as expressing osteoblastic markers and form osteoid in vivo. However, like all the osteosarcomas, the cell population is heterogeneous (Pautke et al., 2004; Cleton-Jansen et al., 2009). After 6 days of culture, the cells were recovered, fixed and permeabilized. After several washes, the cells were incubated with anti-RANKL and anti-HLA-G antibodies (87G) and then analyzed by flow cytometry in order to quantify the simultaneous expressions of RANKL and of HLA-G (intracellular and membrane forms). The data are reported in diagrams A and B (mean of the ratios of the fluorescence intensity or rMFI) and the histograms C and D. Number of experiments performed: n=4.

EXAMPLE

Inhibition In Vitro of the Osteoclasts by the Isoforms of HLA-G

1) Materials and Methods
   a) Mesenchymal Stem Cells (MSC)
   The mesenchymal stem cells are obtained from punctures of iliac crest bone marrow. They were obtained from healthy volunteer patients admitted in the orthopedics-traumatology department of the Centre Hospitalier Universitaire Trousseau (Tours, France) for the implantation of total hip replacement. The patient's written consent was obtained.
   b) Osteosarcoma Lines
   The five osteosarcoma lines MG-63, Cal-72, HOS, U2OS and SaOS2 are well known to persons skilled in the art. They have been described by Billiau et al. (1977), Rochet et al. (1999), Fogh et al. (1975), Ponten and Saksela (1967) and Rhim et al. (1975).
   c) Peripheral Blood Lymphocytic Cells (PBL)
   Blood was collected from healthy volunteers at the Etablissements Francais du Sang (French Establishments for Blood) (Tours, France). Whole blood mononuclear cells (MNC) (PBMC or "Peripheral Blood Mononuclear Cells") were obtained after separation on Ficoll gradient, and the cell ring was then cultured overnight in order to remove the adherent monocytes. After enumeration, the nonadherent PBLs ("Peripheral Blood Lymphocytes") contained in the supernatant were used for the cocultures.
   d) B-EBV Cells
   The B-EBV cells are B cells transformed with the Epstein Barr virus. They are described by Sauce et al. (2004).
   e) $CD14^{pos}$ Cells
   $CD14^{pos}$ cells were selected from PBMC using the purification kit Miltenyi CD14 microbeads kit (Myltenyi; Bergisch Gladbach, Germany) according to the recommendations of the supplier.
   f) Cell Culture and Selection After transport, packaged in citric acid dextrose (CAD), the bone marrow samples were directly placed in culture flasks (BD Biosciences, VWR, Strasbourg, France). The culture medium was changed every 48 hours. The nonadherent cells were removed. After 7 to 15 days of culture, the adherent cells reaching confluence were detached using 0.5% (v/v) of trypsin (In Vitrogen, Fischer Bio Block Scientific, Illkirch, France) and then suspended so as to be characterized or reinoculated at 200 000 cells/cm² for a new proliferation. The cells were maintained in incubators in a humid atmosphere with 5% CO2 and at a temperature of 37° C.
   g) Culture Media
   Proliferation Media
   The proliferation medium used is composed of alpha Minimal Essential Medium (αMEM) (In Vitrogen), 10% fetal calf serum (FCS) (Perbio Hyclone, Logan, United States), 1% penicillin-streptomycin and L-glutamin (In Vitrogen) and fungizone (Bristol Myers Squibb, Rueil Malmaison, France). The osteosarcomatous lines were cultured in this same medium.
   Osteocyte Differentiation Medium
   This medium is composed of αMEM, $0.05 \times 10^{-3}$ M ascorbic acid, $10 \times 10^{-3}$ M β-glycerophosphate (Sigma Aldrich, Lyon, France) and 50 ng/ml of BMP4 (R&D Systems, Minneapolis, Minn.). It allows osteocyte differentiation after 14 days of culture.
   Osteoclast Induction Medium
   $CD14^{pos}$ cells were cultured in 96-well plates containing medium supplemented with M-CSF 25 ng/ml and RANKL 30 ng/ml (R&D Systems) for 15 days. Quantification of the number of multinucleated cells adhering to the bottom of the wells and positive for TRAP was performed at 20 days. The TRAP activity was detected using the TRAP assay kit (Sigma). Medium packaged by the M8-HLA-G5 or M8-control vector lines (Naji et al., 2007a and 2007b) or recombinant human HLA-G5 (rhHLA-G5; Biovendor, Modrice, Czech Republic) could be added to the osteoclast induction medium.
   Dendritic Cell Differentiation Medium
   $CD14^{pos}$ cells derived from PBMC were cultured in medium containing 50 ng/ml of rhGM-CSF and 20 ng/ml rhIL-4 (R&D Systems) for 6 days. This constituted the positive control medium (MONO). To fractions of $CD14^{pos}$ cell medium were added either supernatant of MSC with a control antibody or with the anti-HLA-G blocking antibody (87G) (Exbio, Vestec, Czech Republic). After 6 days of culture, the cells were harvested and analyzed by flow cytometry.
   h) Flow Cytometry
   To detect a membrane antigen, 200 000 living cells are labeled with a specific monoclonal antibody coupled with a fluorochrome. To detect an intracellular antigen, the cells are fixed and permeabilized using the Cytofix/Cytoperm™ kit (Becton Dickinson, Erembodegem, Belgium) following the recommendations of the supplier. The labeling was obtained after 30 minutes of incubation at 4° C. in the dark. The cells were then rinsed with Phosphate Buffered Saline (PBS), and then fixed with CellFIX® (Becton Dickinson). The cells were then run through a flow cytometer (FACS Calibur®, Becton Dickinson), equipped with an argon laser emitting at a wavelength of 488 nm. The data were analyzed using the CellQuest 3.1® software (Becton Dickinson). The results are expressed as a ratio of mean fluorescence intensity (RMFI) of the signal detected relative to that of the background noise. To detect HLA-G, the antibodies used were those produced by the 87G clone conjugated with Alexa488 (recognizing the HLA-G1 and -G5 isoforms), the MEM/G9 clone conjugated with APC (also recognizing the HLA-G1 and -G5 isoforms) and the 5A6G7 clone conjugated with Alexa488 (recognizing the HLA-G5 and -G6 isoforms) (Exbio). To detect RANKL, the antibody used was that produced by the MIH24 clone (eBioscience; San Diego, Calif.). To detect ILT2, the antibody used was that produced by the VMP55 clone (Santa Cruz Biotechnology, Santa Cruz, Calif.). To detect ILT4, the antibody used was that produced by the 42D1 clone (Santa Cruz Biotechnology). To detect CD14, the antibody used was that produced by the 134620 clone (R&D Systems). To detect CD1a, the antibody used was that produced by the HI149 clone (Becton Dickinson).

i) Confocal Microscopy

The cells to be examined were inoculated into well chambers with a surface area of 1 cm$^2$ on slides (Labteks®, Nunc International, Rochester, N.Y., USA) at 10 000 cells/well. After 48 hours of culture, they were fixed for 10 minutes with 4% paraformaldehyde (Sigma). A permeabilization step with a solution of PBS, 0.5% FCS and 0.1% tritonX100 (BioRad, Hercules, Calif., USA), for 5 minutes at room temperature, was necessary in order to identify the intracellular proteins. The cells were then successively incubated with phosphorylated anti-tyrosine (4G10, Millipore, Billerica, Mass.) or anti-SHP-1 (R&D Systems) primary antibodies, for 1 hour at 4° C. and the corresponding secondary antibodies conjugated with a fluorochrome of the Alexa 488 or 594 type (In Vitrogen). After rinsing, a mounting medium (Vector Cliniscience, Montrouge, France) was added. Wells containing control antibodies served as negative controls. The slides were examined under a confocal microscope (Olympus, Fluoview™ FV1000; Hamburg, Germany).

j) Mixed Lymphocyte Culture (MLR):

The mixed lymphocyte cultures were prepared on a 96-well plate. The PBLs (responding cells) were inoculated at the rate of 10$^5$ cells. The B-EBVs (stimulating cells) were irradiated (75 Gy) and used at 5×10$^4$ cells. The MSCs were cocultured at the rate of 5×10$^4$ cells. BMP4 was used at a concentration of 20 ng/ml on D0 and D3. After 6 days of coculture, the incorporation of Brdu (5-bromo-2'dioxyuridine) was monitored by means of an anti-Brdu antibody coupled with europium (Perkin Elmer, Waltham, Mass.). The quantity of europium was measured using the Delfia proliferation kit (Perkin Elmer). The fluorescence of the europium observed by DELFIA (Dissociation-Enhanced Lanthanide Fluorescent Immunoassay) is proportional to the DNA synthesized and therefore to the lymphocyte proliferation. In some experiments, phytohemagglutinin (PHA) (R&D Systems) at 10 µg/ml was used to activate the PBLs.

k) Immunoprecipitation

The µMACS™ Protein A/G Microbeads kit (Miltenyi) was used to carry out the immunoprecipitations. The cell samples were treated according to the recommendations of the supplier. After elution of the fraction not retained, the immunoprecipitated protein samples were analyzed by Western blotting.

l) Western Blotting

The cells (1×10$^6$ cells) were lysed in a specific buffer (Lysis Buffer): 1% Sodium Dodecyl Sulfate (SDS) (Sigma), 1 mM sodium orthovanadate (Sigma), 10 mM Tris pH 7.4 (Sigma) supplemented with an antiprotease solution (Roche Diagnostic, Mannheim, Germany). The samples were assayed by the mini kit BCA Pierce (Pierce, New York, USA). The concentration was evaluated by spectrophotometry at 562 nm. The samples intended to be analyzed by Western blotting were added to 1× sample buffer composed of 0.0625 M TRIS, 2% SDS, 20% glycerol, 0.01% Bromophenol Blue, 0.2% β-Mercapto-ethanol, and placed for 3 minutes at 95° C. A gel was prepared on a mounting kit (Bio-rad, California, USA). A separating gel containing 10% acrylamide (Acrylamide bisacrylamide 37.5/1 at 40%) composed of separating buffer 1.5 mM Tris HCl pH 8.8, 10% acrylamide, 0.012% TEMED (N,N,N,N-Tetramethyl-Ethylenediamine; Sigma) and 0.05% APS (ammonium persulfate; Sigma) was poured and a second concentrating gel containing 4% acrylamide composed of concentrating buffer (0.5 mM Tris HCl pH 6.8, 4% acrylamide, 0.1% SDS, 0.03% TEMED and 0.05% APS), was deposited on top. After polymerization, the samples were deposited at the rate of 10 to 20 µg per well as well as a molecular weight marker (Precision Plus Protein Standards, Bio-rad). The migration was performed successively for 15 minutes at 70 mV, 5 minutes at 100 mV and at 120 mV until the end of the migration in a migration buffer (25 mM Tris, 0.19 M glycine and 1% SDS). The transfer material (Mini protean II; Bio-rad) as well as the acrylamide gel were equilibrated in transfer buffer composed of 2% previously prepared migration buffer and 5% methanol. The transfer was performed on a 0.45 µm nitrocellulose membrane (Protran BA85 cellulosenitrate, Schleicher & Schull, Dassel, Germany) hydrated beforehand for 2 hours, at 250 mA in transfer buffer. After the transfer, the membranes were saturated with PBS Tween 0.1% (Sigma), 5% milk (skimmed, low in calcium) for 1 h at room temperature. The membranes were incubated with primary anti-SHP-1 antibodies (R&D Systems) diluted in PBS Tween 0.1%, 5% milk, overnight at 4° C. Anti-goat rabbit antibodies coupled with HRP (Horse Radish Peroxydase) (Jackson ImmunoResearch, West Grove, Pa., USA) were used as secondary antibodies. The incubation was performed at room temperature for 2 hours. The membranes were incubated with the HRP substrate (Opti-4CN substrate kit; Bio-Rad) until stained bands were obtained.

m) Analyses by ELISA (Enzyme Linked ImmunoSorbent Assay)

The concentrations of HLA-G and RANKL secreted in the supernatants of various cell cultures prepared were measured. The ELISA kits for assaying HLA-G5 (Exbio) and RANKL (Biovendor) were used according to the recommendations of the supplier.

2) Results

It has been reported in the literature that osteoclastic cells could be obtained from peripheral blood monocytes or dendritic cells. It is also known that monocytic cells express the HLA-G ILT2 and ILT4 receptors at their surface.

A study was carried out on whether the expression of the ILT2 and ILT4 receptors of HLA-G by the monocytic cells was preserved when these cells are cocultured with MSCs of bone marrow and whether the latter could express them.

After about 6 days of culture, the flow cytometry data (see FIG. 1) showed that only the CD14$^{pos}$ monocytic cells expressed ILT2 and ILT4 and that these expressions were indeed maintained over time.

It was then examined if HLA-G could inhibit osteoclast differentiation during the differentiation of monocytes into dendritic cells or during osteoclastogenesis from monocytes.

CD14$^{pos}$/CD1a$^{neg}$ peripheral blood monocytes were stimulated with GM-CSF and IL4 in order to obtain CD14$^{neg}$/CD1a$^{pos}$ dendritic cells. The additions of MSC culture supernatants inhibited the differentiation of the cells (the majority were CD14$^{pos}$/CD1a$^{neg}$) unlike the control conditions where the majority of the cells became CD14$^{neg}$ including a fraction expressing CD1a. The addition of anti-HLA-G blocking antibody (87G) partially lifted the inhibition observed with the MSCs since cells expressing CD1a were detected (see FIG. 2).

CD14$^{pos}$ monocytes were then induced to differentiate directly into osteoclasts after addition of M-CSF and RANKL (positive control conditions). Under certain conditions there were added i) supernatants of media packaged by an M8 line transfected or otherwise with cDNA encoding HLA-G5 (G5 MC and MC Ctrl respectively) or ii) recombinant human HLA-G5 (rh G5).

Whereas under positive controls and under MC Ctrl conditions, osteoclasts were easily observed, few were observed under G5 MC conditions (see FIG. 3). Under conditions where recombinant HLA-G5 was used, osteoclasts were rarely detected. HLA-G5 is therefore capable of inhibiting the generation of osteoclasts from monocytes.

It is known that the ILT2 and ILT4 receptors have ITIM motifs in their intracytoplasmic part. These motifs are capable of activating SHP-1 type phosphatases at the level of tyrosines when these receptors are bound to their ligand (Barrow and Trowsdale, 2006).

The activation of SHP-1 in normal $CD14^{pos}$ monocytic cells or the THP-1 line was therefore evaluated. These cells were incubated with beads coated with HLA-G or beads alone as negative control. The beads were obtained according to the method described by Naji et al. (2007a).

The results presented in FIG. 4 show a net increase in phosphorylated SHP-1 when the cells are brought into contact with $HLA-G^{pos}$ beads, this being regardless of the type of monocytic cells (THP-1 or $CD14^{pos}$ cells) (see FIG. 4A). Moreover, when $CD14^{pos}$ monocytes are cocultured with MSCs, colocalization of the expression of phosphorylated tyrosines and SHP-1 was observed (see FIG. 4B). These data show that HLA-G induces the activation of proteins inhibiting the differentiation of monocytic cells.

Osteoclastogenesis is dependent on the RANKL molecule. The latter may be secreted mainly by lymphocytic cells and by the osteoblasts themselves. It was therefore examined whether there was a link between the expression of HLA-G and of RANKL.

FIG. 5A shows that the MSCs are capable of inhibiting the proliferation of lymphocytes under mixed lymphocyte culture conditions. The addition of the BMP4 need not increase this effect.

The secretion of RANKL in supernatants of these cocultures was next quantified. It was observed that under each condition containing MSCs, there was a significant decrease in the secretion of RANKL and this even when the lymphocytes were activated by PHA (see FIG. 5B). These results suggest that the inhibition of the activation of the lymphocytes by the MSCs also reduces the secretion of RANKL.

It has previously been shown by some of the inventors that this inhibition was partly due to HLA-G and that the interaction between allogenic lymphocytes and MSC induced the release of HLA-G into the culture medium (Selmani et al., 2008).

It was therefore checked if an inverse relationship existed between the expression of HLA-G and RANKL. MSCs were induced to produce RANKL by inducing osteoblastic differentiation. Indeed, it is known that osteoblasts produce RANKL (Lorenzo et al., 2008). Osteoblastic differentiation reduced the expression of HLA-G1 and HLA-G5 in the MSCs and concomitantly increased the expression of RANKL (see FIG. 6). This result was confirmed by the ELISA technique since it was possible to detect RANKL in the supernatants of induced cultures (Diff) unlike cultures which were not induced (Undiff).

This relationship was next evaluated in osteoblastic cells derived from osteosarcoma lines. Remarkably, an inverse relationship was also observed between the expression of RANKL and HLA-G. For the CAL-72, HOS, SaOs2 and U2OS lines, the induction of osteoblastic differentiation reduced the expression of HLA-G1 and HLA-G5 and concomitantly increased the expression of RANKL. For the MG-63 line, the differentiation increased the expression of HLA-G and reduced that of RANKL (see FIG. 7).

It is evident from these results that HLA-G expressed by the MSCs or the osteoblastic cells (normal or tumoral) inhibits bone resorption in two ways: either directly by suppressing osteoclastogenesis, or indirectly by inhibiting the activation of the cells secreting RANKL. Moreover, there is an inverse relationship between the expression of HLA-G and RANKL in osteoblastic cells.

BIBLIOGRAPHIC REFERENCES

Barrow A D and Trowsdale J., *Eur J. Immunol.* 2006; 36: 1646-1653
Billiau A, et al., *Antimicrob Agents Chemother.* 1977; 12: 11-15
Carosella E D, et al., *Trends Immunol.* 2008a; 29: 125-132
Carosella E D, et al., *Blood.* 2008b; 111: 4862-4870
Cleton-Jansen A M, et al., *Br J. Cancer.* 2009; 101: 1909-1918
Cohen M M, Jr., *Am J Med Genet A.* 2006; 140: 2646-2706
Deschaseaux F, et al., *Trends Mol. Med.* 2009a; 15: 417-429
Deschaseaux F, et al., *J Cell Mol. Med.* 2009b; 14: 103-115
Duplomb L, et al., *Stem Cells.* 2007; 25: 544-552
Ellis S, *Am J Reprod Immunol.* 1990; 23: 84-86
Fogh, J., et al., in J. Fogh (ed.), Human Tumor Cell Lines in vitro. New York: Plenum Press 1975; 115-159.
Geraghty D E, et al., *Proc Natl Acad Sci USA.* 1987; 84: 9145-9149
Hackmon R, et al., *Fetal Diagn Ther.* 2004; 19: 404-409
Ishitani A and Geraghty D E., *Proc Natl Acad Sci USA.* 1992; 89: 3947-3951
Kirszenbaum M, et al., *Proc Natl Acad Sci USA.* 1994; 91: 4209-4213
Kirszenbaum M, et al., *Hum Immunol.* 1995; 43: 237-241
Le Maoult J. et al., *FASEB J.* 2005; 19: 662-664
Lorenzo J, et al., *Endocr Rev.* 2008; 29: 403-440
Moreau P, et al., *Hum Immunol.* 1995; 43: 231-236
Naji A, et al., *Blood.* 2007a; 110: 3936-3948
Naji A, et al., *Hum Immunol.* 2007b; 68: 233-239
Pautke C, et al., *Anticancer Res.* 2004; 24: 3743-3748
Ponten J and Saksela E., *Int J Cancer.* 1967; 2: 434-447
Rebmann V, et al., *Tissue Antigens.* 1999; 53: 14-22
Rhim J S, et al., *Nature.* 1975; 256: 751-753
Rochet N, et al., *Int J Cancer.* 1999; 82: 282-285
Rouas-Freiss N, et al., *Transplantation.* 2007; 84: S21-25
Sauce D, et al., *Gene Ther.* 2004; 11: 1019-1022
Selmani Z, et al., *Stem Cells.* 2008; 26: 212-222

The invention claimed is:

1. A method of treating bone resorption in a subject suffering from excess bone resorption, comprising administering to the subject a pharmaceutical composition comprising an isolated isoform of HLA-G selected from the group consisting of HLA-G1 and HLA-G5 and at least one pharmaceutically acceptable vehicle, wherein the isoform of HLA-G is in monomeric form.

2. The method of claim 1, wherein the isoform of HLA-G is HLA-G5.

3. The method of claim 1, wherein the subject is suffering from a disease selected from the group consisting of osteoporosis, osteopenia, and Paget's disease.

4. The method of claim 1, wherein the subject is suffering from a bone fracture.

5. The method of claim 1, wherein the subject is suffering from an osteolytic tumor.

6. The method of claim 1, wherein the subject is suffering from a disease selected from the group consisting of osteoporosis, osteopenia, Paget's disease, osteolytic tumor and bone fracture.

7. The method of claim 1, wherein the subject is a human.

* * * * *